US007753915B1

(12) United States Patent
Eksler et al.

(10) Patent No.: US 7,753,915 B1
(45) Date of Patent: Jul. 13, 2010

(54) BI-DIRECTIONAL BONE LENGTH ADJUSTMENT SYSTEM

(76) Inventors: August Eksler, 17 Walton Ct., Newtown, PA (US) 18940; Luiza Blyakher, 288 Bay 38th St., Apt. 6R, Brooklyn, NY (US) 11214; Vladimir Krakhman, 971 Hickory Ridge Dr., Chalfont, PA (US) 18914

( * ) Notice: Subject to any disclaimer, the term of this patent is extended or adjusted under 35 U.S.C. 154(b) by 383 days.

(21) Appl. No.: 11/818,457

(22) Filed: Jun. 14, 2007

(51) Int. Cl.
*A61B 17/58* (2006.01)

(52) U.S. Cl. .......................... 606/105; 606/63; 606/258; 606/86 R; 623/18.12

(58) Field of Classification Search ............... 606/54, 606/55, 56, 57, 58, 59, 62, 63, 64, 65, 66, 606/67, 68, 69, 105, 86 R, 258; 623/18.12; 403/109.7; 310/163–164; 335/228; 600/407, 600/424
See application file for complete search history.

(56) References Cited

U.S. PATENT DOCUMENTS

| | | | | |
|---|---|---|---|---|
| 3,915,151 A | * | 10/1975 | Kraus | 600/13 |
| 3,976,060 A | * | 8/1976 | Hildebrandt et al. | 606/241 |
| 4,475,546 A | * | 10/1984 | Patton | 606/57 |
| 4,611,586 A | * | 9/1986 | Agee et al. | 606/55 |
| 5,626,579 A | * | 5/1997 | Muschler et al. | 606/60 |
| 6,311,082 B1 | * | 10/2001 | Creighton et al. | 600/407 |
| 6,500,177 B1 | * | 12/2002 | Martinelli et al. | 606/57 |
| 6,663,617 B1 | | 12/2003 | Vito et al. | |
| 6,678,562 B1 | | 1/2004 | Tepper et al. | |
| 6,699,176 B1 | | 3/2004 | Khouri | |
| 6,706,042 B2 | | 3/2004 | Taylor | |
| 6,849,076 B2 | * | 2/2005 | Blunn et al. | 606/105 |
| 6,899,669 B2 | | 5/2005 | Vito et al. | |
| 6,899,680 B2 | | 5/2005 | Hoff et al. | |
| 6,964,663 B2 | | 11/2005 | Grant et al. | |
| 6,991,628 B2 | | 1/2006 | Vito et al. | |
| 7,018,402 B2 | | 3/2006 | Vito et al. | |
| 7,135,022 B2 | * | 11/2006 | Kosashvili et al. | 606/63 |
| 7,481,841 B2 | * | 1/2009 | Hazebrouck et al. | 623/18.12 |
| 2003/0032958 A1 | * | 2/2003 | Soubeiran | 606/61 |
| 2004/0030395 A1 | * | 2/2004 | Blunn et al. | 623/18.12 |
| 2006/0004459 A1 | * | 1/2006 | Hazebrouck et al. | 623/18.12 |
| 2006/0047282 A1 | * | 3/2006 | Gordon | 606/61 |
| 2007/0260105 A1 | * | 11/2007 | Uchiyama et al. | 600/12 |
| 2009/0204154 A1 | * | 8/2009 | Kiester | 606/258 |

\* cited by examiner

*Primary Examiner*—Eduardo C Robert
*Assistant Examiner*—Jan Christopher Merene
(74) *Attorney, Agent, or Firm*—Brian Roffe

(57) ABSTRACT

Bone length adjustment method and system includes a two-part telescopic device connected to bone parts whose length between the connection points is to be adjusted, with each part of the telescopic device being secured to the bone part, and a rod with an embedded permanent magnet which is in threaded engagement at one or both of its ends with one or both of the parts of the telescopic device. The permanent magnet in the rod is excited by an external solenoid arrangement to cause a radial force to develop at the rod thereby causing it to rotate. Rotation of the rod is converted via the threads at one or both of its ends to axial motion or movement of the telescopic parts relative to each other and thereby causes an increase or decrease in the bone length depending on the direction of axial movement between the telescopic parts.

25 Claims, 16 Drawing Sheets

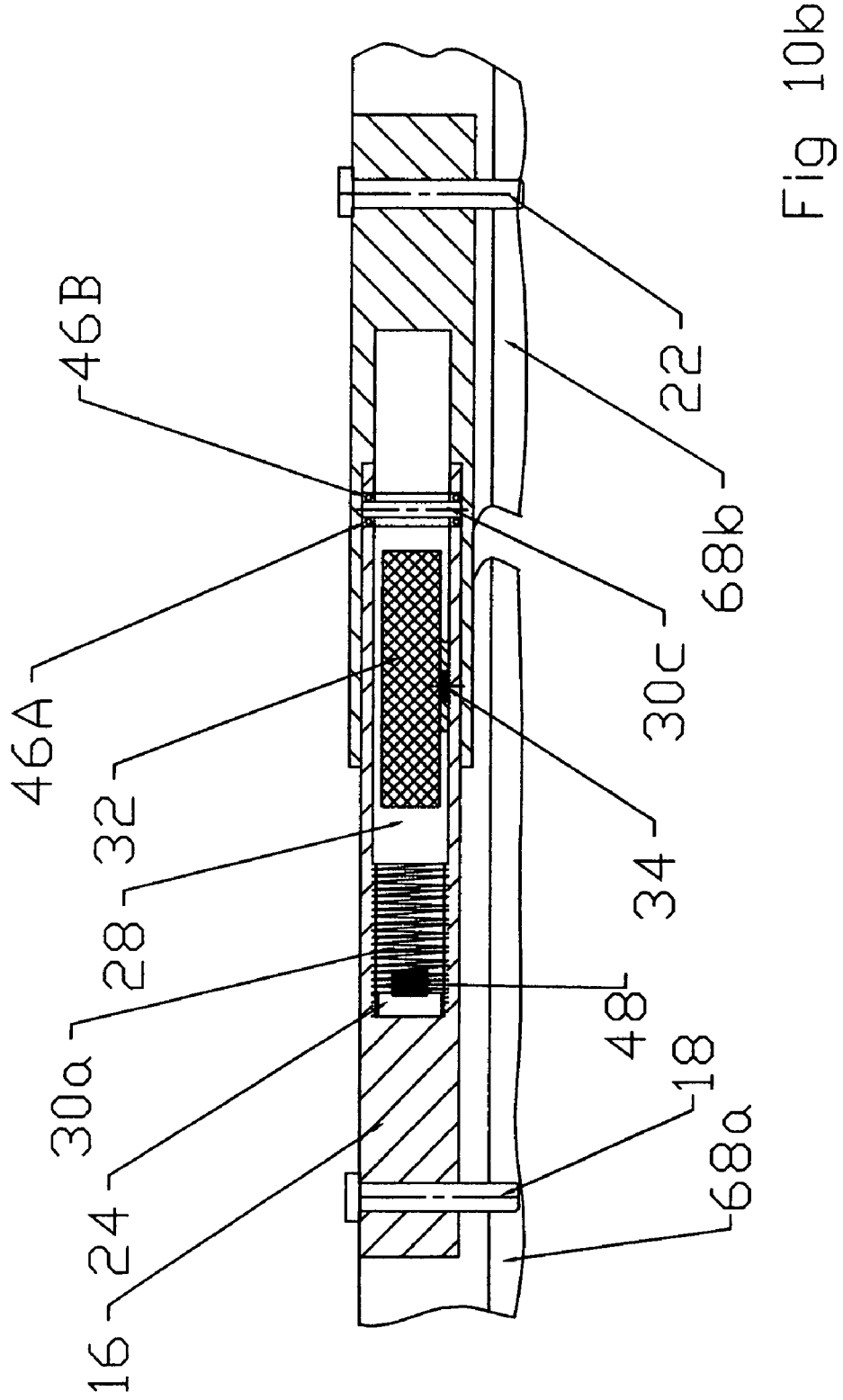

BI-DIRECTIONAL BONE LENGTH ADJUSTMENT SYSTEM

FIELD OF THE INVENTION

The present invention relates generally to a bone length adjustment system having a first part arranged in connection with a bone whose length is to be adjusted and a second actuating part which magnetically interacts with the first part to cause the bone length adjustment.

The present invention also relates independently to an electro-magnetically actuated, telescopic implant for use in healing fractured bones and bone length adjustment.

The present invention also relates independently to a bi-directional bone length adjustment system which is capable of adjusting its length in increments to provide either an increase or decrease in length, which adjustment is potentially effected under the influence of an electromagnetic field generated outside of the body in which the bone is located.

BACKGROUND OF THE INVENTION

A typical device used for bone lengthening consists of a special internal lengthening nail, such as a skeletal kinetic distractor implanted in a cavity formed by the removal of the bone marrow from, for example, a leg bone. This device usually includes two telescopic sections pinned to each end of the broken bone and it is axially extendable, which extension is caused by small oscillations between the two telescopic sections which are mechanically converted to a one-way distraction (axial lengthening). Such a device utilizes the motion of the patient limb, for example, manually or during walking, to cause lengthening of the bone. A main drawback of this device is the lack of control over the lengthening of the bone, which may cause an adverse increase in the bone length.

Another device proposed for bone lengthening is a two-part telescopic orthopedic device which is inserted into a medullary cavity of a fractured bone, with each part of the telescopic device being secured to a respective end of the bone. One of the telescopic sections comprises a ferromagnetic material or permanent magnet, which is actuatable by an external axially directed magnetic field, such that one section may be caused to move axially in relation to the other section upon application or exposure to the magnetic field. One weakness of this device is that it provides for an essentially unidirectional motion, which can provide only an increase in length of the bone, but cannot be used to provide bone compression, i.e., a decrease in the length of the bone.

It would therefore be beneficial to provide a bi-directional bone length adjustment device, apparatus, system and method for using the same which can be installed in connection with a fractured bone and can be controlled to both lengthen and compress the bone to provide either an increase in bone length or a decrease in bone length.

OBJECTS AND SUMMARY OF THE INVENTION

It is a general object of one or more embodiments of the invention to provide a new and improved bone length adjustment system.

It is an object of one or more embodiments of the invention to provide a simplified, reliable implantable bone length adjustment device which moves the ends of a broken bone either away from each other or toward each other while maintaining the end regions of the fractured bone in alignment.

It is another object of one or more embodiments of the invention to provide an implantable device which is capable for use to correct spine deformation by distraction or compression of the entire spine or part of the spine.

It is yet another object of one or more embodiments of the invention to provide a bone length adjustment system which is capable of lengthening and correcting deformation of flat bones by providing distraction or compression of these flat bones while the lengthening mechanism is located outside of the engaged parts of the corrected bone.

It is a further object of one or more embodiments of the invention to provide an external mechanism for activating an implantable bone length adjustment device.

It is still another object of one or more embodiments of the invention to provide a bone length adjustment device which is implantable entirely within a bone and which does not require external force, such a patient limb motion, to achieve bone length adjustment.

It is still a further object of one or more embodiments of the invention to provide an implantable bone length adjustment apparatus capable of controlling bone length adjustment automatically based on a pre-programmed long or short-term profile, including compression or distraction or a combination of both, based on a periodic or non-periodic time schedule.

In order to achieve one or more of the foregoing objects and possibly others, a first embodiment of a bone length adjustment system in accordance with the invention includes a two-part telescopic orthopedic device connected to the bone, or bone parts whose length between the connection points is to be adjusted, with each part of the telescopic device being secured to the bone or bone part, and a rod with an embedded permanent magnet which is in threaded engagement at one or both of its ends with one or both of the parts of the telescopic device. The permanent magnet in the rod is excited by an external solenoid arrangement to cause a radial force to develop at the rod thereby causing it to rotate. Rotation of the rod is converted via the threads at one or both of its ends to axial motion or movement of the telescopic parts relative to each other and thereby causes an increase or decrease in the bone length depending on the direction of axial movement between the telescopic parts. The direction of motion depends, for example, on a commutation sequence of the external coils. Other mechanisms for converting the rotation of the rod into axial movement of the telescopic parts relative to one another are also envisioned.

The telescopic device may be inserted into a medullary cavity of a fractured bone, attached to a side or edge of the fractured bone or to multiple bones while being implanted within the body (underneath skin) or connected to a side or edge of a fractured bone or to multiple bones while being exterior of the body.

A bone length adjustment system in accordance with the invention therefore forms a novel medical apparatus which allows flexible remote control for compression and distraction of bones under any pattern combination of compression and distraction, with any time increments and at any variable, desired incremental length adjustment during the bone lengthening procedure. It allows for bone adjustment of elongated bone, as well as for correction of spine deformation and surgical reconstruction of bones.

BRIEF DESCRIPTION OF THE DRAWINGS

The following drawings are illustrative of embodiments of the invention and are not meant to limit the scope of the invention as encompassed by the claims.

FIGS. 2, 2a and 2b show enlarged views of a portion around a magnet of the telescoping device shown in FIG. 1a.

FIG. 10b is a cut-away view of the implantable part of the bone length adjustment system shown in FIG. 10a.

DETAILED DESCRIPTION OF THE PREFERRED EMBODIMENTS

Figure 1A:
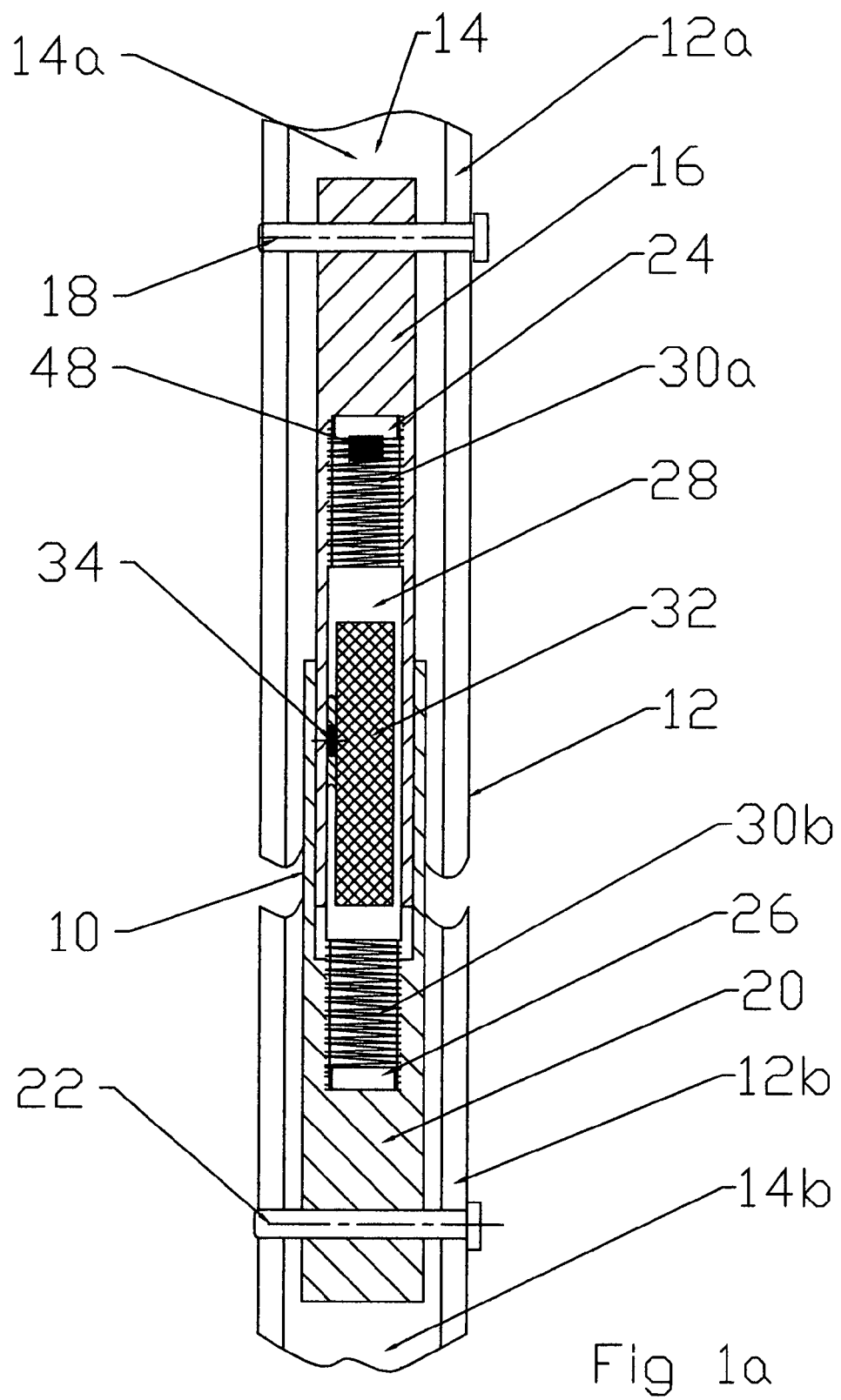
FIG. 1a is a cross-sectional view of a first embodiment of an implantable, telescoping intramedullary device inserted into a medullary cavity of a fractured bone.

Referring to the accompanying drawings wherein like reference numerals refer to the same or similar elements, one embodiment of a bone length adjustment system in accordance with the invention includes two parts, one implantable in connection with a fractured bone, e.g., in a cavity in the bone, or two separate bones and the other external of the bone or bone parts and preferably external of the body in which the bone or bone parts are situated. Several implantable parts are disclosed below and several external parts are disclosed below. Any of the implantable parts can be used with any of the external parts. Further, the implantable parts disclosed herein are only preferably used in combination with any of the external parts disclosed herein and can also be used independent thereof and possibly in connection with other external or internal parts to achieve bone length adjustment. Similarly, the external parts disclosed herein are only preferably used in combination with any of the internal parts disclosed herein and can be used independent thereof and possibly in connection with other external or internal parts to achieve bone length adjustment.

FIG. 1a shows one embodiment of the implantable part of the bone length adjustment system in accordance with the invention, designated generally as 10, which can be used for adjusting the length of a bone 12 having an intramedullary cavity 14. The implantable part 10 is operatively situated in the intramedullary cavity 14 of a bone 12. For a bone fractured such that part of the intramedullary cavity 14 is on both sides of the fracture as shown, there are intramedullary cavity parts 14a, 14b. One part of the implantable part 10 is situated in each cavity part 14a, 14b.

The implantable part 10 includes a two-part telescopic device having a first part 16 connected to a portion 12a of the fractured bone 12 by a suitable attachment mechanism such as a nail 18 as shown, and a second part 20 connected to a portion 12b of the fractured bone 12 by a suitable attachment mechanism such as a nail 22 as shown. Other attachment mechanisms or mechanisms for fixing the first and second parts 16, 20 of the part 10 to the bone portions 12a, 12b are also envisioned, such as biocompatible screws.

The first and second parts 16, 20 are arranged telescopically, i.e., such that they are movable axially relative to one another. They are also preferably connected to provide a telescopic interaction. The first part 16 is a core-like part and the second part 20 is a socket-like part, i.e., the cross-sectional dimensions of the first part 16 are less than the cross-sectional dimensions of the second part 20 such that a portion of the second part 20 can surround the first part 16.

Both first and second telescoping parts 16, 20 are capable of sliding axially in the cavity 14, i.e., the first part 16 is capable of sliding relative to the second part 20 while the second part 20 remains stationary and the second part 20 is capable of sliding relative to the first part 16 while the first part 16 remains stationary. The first and second parts 16, 20 can also both slide simultaneously. The part or parts which slides depend on the manner in which a rod is connected to the parts 16, 20, discussed below.

The first part 16 has a cavity facing the second part 20 and an axial, threaded channel 24 is formed at an inner end of this cavity. The second part 20 has a cavity facing the first part 16 and an axial, threaded channel 26 is formed at an inner end of this cavity with the threaded channel 26 having an opposite direction of threads than the direction of the threads forming threaded channel 24.

A substantially cylindrical rod 28 is arranged in the cavities of the first and second telescoping parts 16, 20 and connects the parts 16, 20 together. Rod 28 has axial, threaded portions at each end 30a, 30b with opposite directions of threads to enable threaded portion 30a to be engaged with threaded channel 24 and threaded portion 30b to be engaged with threaded channel 26. Thus, as rod 28 rotates in one direction, the first and second parts 16, 20 will both either move axially in a direction away from the center of the rod 28 or move axially in a direction toward the center of the rod 28. Other mechanisms and techniques for coupling the rod 28 to the first and second parts 16, 20 to provide for translation of rotational movement of the rod 28 into axial movement of the first and second parts 16, 20 are also envisioned to be within the scope and spirit of the invention.

The telescoping first and second parts 16, 20 and the rod 28 should be made from non-magnetic material, such as synthetic plastic composition, steel alloy or titanium.

A permanent magnet 32 is arranged in connection with the rod 28, e.g., arranged in a cavity or opening in the rod 28, or possibly embedded in or otherwise fixed to the rod 28. Thus, for example, magnet 32 may be situated inside of the threaded rod 28 and attached to the threaded rod 28 by, for example, gluing it to the surfaces defining the cavity in the body of the rod 28 or fixed in position using a setscrew 34. Other mechanisms for attaching the magnet 32 to the interior surfaces of the rod 28 defining the cavity or for arranging the magnet 32 in connection with the rod 28 are also envisioned. Whatever connection mechanism is used should ensure that the rod 28 and magnet 32 are rotationally coupled to one another to one another so that rotation of the magnet 32 causes rotation of the rod 28.

Figure 2:
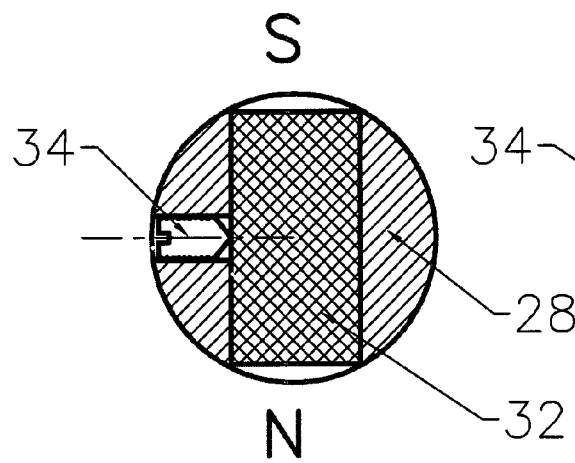
Figure 2:
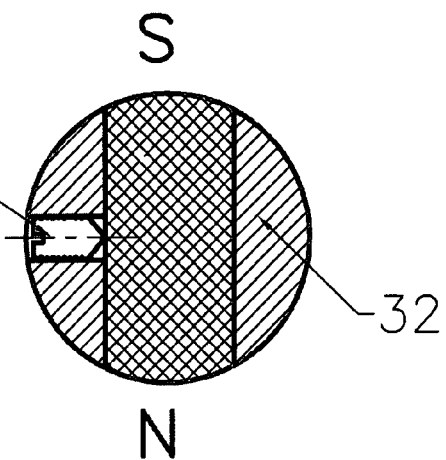
Figure 2:
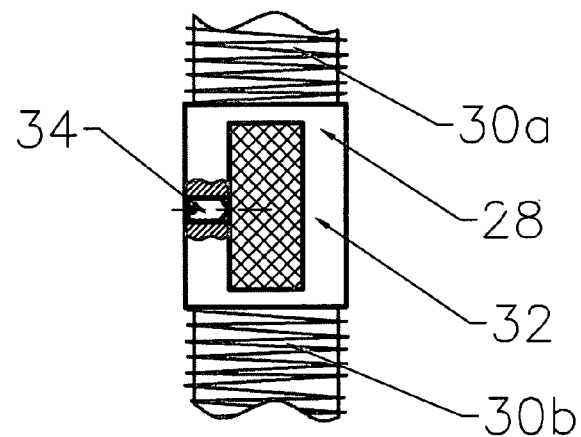

Magnet 32 is preferably fabricated from a ferromagnetic material and arranged such that the two magnetic poles, North and South, are located on the two sides facing the opening in the threaded rod 28 as shown in FIGS. 2*a* and 2*b*. The pole side of the permanent magnet 32 may be implemented as a rectangular shape as shown in FIG. 2*a* or with two, rounded pole sides as shown in FIG. 2*b*. Magnet 32 may also be arranged in connection with the rod 28 as shown such that an axis between its poles is substantially parallel to an axial axis of the rod 28.

In order to prevent the threaded rod 28 from moving by itself, or on its own, under a large axial load, the threaded rod 28 preferably has a buttress implementation, the purpose of which is described below. Other constructions of the threaded rod 28 may be used to prevent it from moving on its own as well as to prevent it from moving when not under the influence of a dynamic rotational magnetic field, the generation of which is described below.

Figure 3:
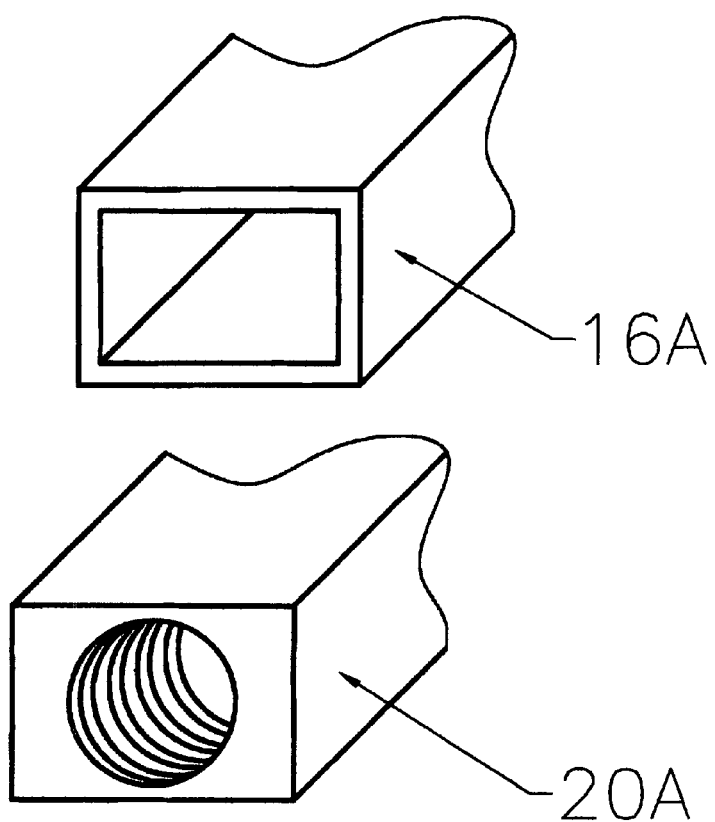
FIG. 3 shows an alternative embodiment of the two-part telescopic intramedullary orthopedic device.

In the embodiment shown in FIG. 1*a*, the first and second parts 16, 20 of the telescopic device of the implantable part 10 are cylindrical, i.e., they have a generally circular cross-sectional form. The second part 20 thus has a cylindrical cavity facing the distant end of first part 16 and into which a portion of the first part 16 is situated and in which cavity the first part 16 partly slides. However, as shown in FIG. 3, in another embodiment of the invention, the first and second parts 16A, 20A may have a non-circular cross-sectional form, e.g., a rectangular cross-sectional as shown. Other non-circular cross-sectional forms are also envisioned for the first and second telescoping parts including, for example, a square cross-sectional form. A non-circular cross-sectional shape of the first and second parts 16A, 20A inhibits or even prevents rotation of the first and second parts 16A, 20A and thereby provides rigidity to and stable alignment within the fractured bone. Further, the first and second parts are not required to have the same cross-sectional form and in they differ, the cavity in the second part must be dimensioned to slidingly accommodate the first part.

Regardless of the cross-sectional form of the first and second parts, the cavity in the first and second parts 16A, 20A into which the rod 28 is inserted may be cylindrical, in view of the preferred shape of the rod 28 which is cylindrical. Nevertheless, the cavities and rod may have other cross-sectional shapes.

Figure 1B:
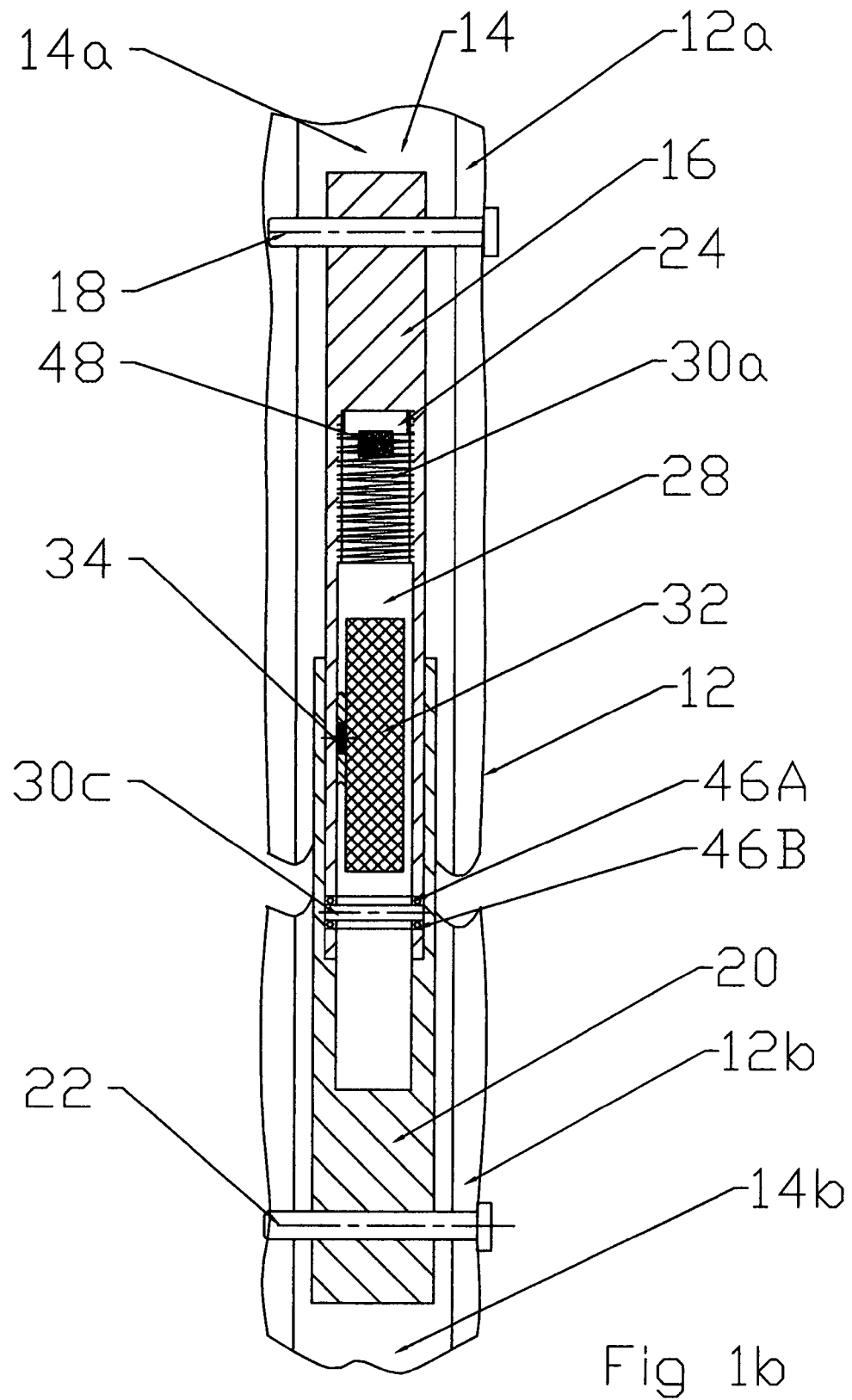
FIG. 1b is a cross-sectional view of a second embodiment of an implantable, telescoping intramedullary device inserted into the medullary cavity of a fractured bone.

As an alternative to the presence of a threaded rod 28 having threaded portions 30*a*, 30*b*, one at each end as shown in FIG. 1*a*, a threaded rod 28A can be formed which has only a single threaded end 30*a* as shown in FIG. 1*b*. The second end of the threaded rod 28A does not have a threaded portion but instead has a shoulder 30*c*. Shoulder 30*c* is engaged with two, preferably low friction bearings 46A and 46B, which are attached to the second telescopic part 20. In this embodiment, rotation of the permanent magnet 32 is converted to linear motion of the threaded rod 28 whereby the shoulder 30*c* pushes or pulls the bearings 46A or 46B and provides a separation or compression of two ends of fractured bone 12. This embodiment may be particularly useful when the size of the telescopic parts 16, 20 is a critical concern and/or when it is desired to have a small bone length adjustment increment.

In the embodiments shown in FIGS. 1*a* and 1*b*, there is a single permanent magnet 32. However, it is envisioned that for some applications which require a large driving force for bone adjustment, the number of permanent magnets, and associated solenoids, can be increased to two or more, the number being limited primarily only by available space. For example, a second permanent magnet (not shown) can be provided in connection with the threaded rod 28 and situated either below or above the first permanent magnet 32. Both permanent magnets may have identical magnetic field orientation or alternatively, may have an angle shift which minimizes interference between magnetic fields generating by solenoid arrangements. Alignment between all permanent magnets and associated or corresponding solenoids may be identical to that described for a single permanent magnet and associated solenoids.

The external part of the bone length adjustment system in accordance with the invention is intended to be used in particular in conjunction with the implantable part 10 and generates a magnetic field which causes the permanent magnet 32 to rotate, resulting in movement of the telescoping first and/or second parts 16, 20 axially or longitudinally relative to one another. The magnetic field is generated preferably by means of solenoids combined in a structure which creates a dynamically moving magnetic field around the permanent magnet 32, in either a clockwise or counterclockwise direction. The externally generated, dynamically moving magnetic field creates a radial force which interacts with or effects the permanent magnet 32 and develops a force causing the magnet 32, and thus the threaded rod 28 rotationally coupled thereto, to rotate. Rotation of the rod 28 caused by rotation of the magnet 32 causes axial or longitudinal movement of the first and/or second parts 16, 20 relative to one another, i.e., the rotation of the rod 28 is converted or translated into linear axial movement of the first and/or second parts 16, 20 relative to one another. Thus, the creation of a magnetic rotational field around the magnet 32 starts a series of movements resulting in axial or longitudinal movement of the first and/or second parts 16, 20 relative to one another. This axial or longitudinal movement may be the outward movement of both first and second parts 16, 20 relative to the magnet 32 to inward movement of both first and second parts relative to the magnet 32.

A bone length adjustment system in accordance with the invention therefore utilizes physical phenomena of the properties of a magnetic field to achieve the bone length adjustment. As known to practitioners using magnetic fields, two permanent magnets exert a force on one another. Each magnet presents a dipolar nature, i.e., each magnet has two poles, called North and South. If two North poles (or South poles) are brought near, a repulsive force is produced. If a North pole and South pole are brought near, then an attraction force is produced.

The solenoids which create the dynamically moving magnetic field may be enclosed into a modular form or frame to allow for an easy and convenient way to provide effective treatment for a patient. In one embodiment, the solenoid module may be equipped with a mechanism for removing excessive heat produced during operation. For example, this mechanism may be a cooling system which is constructed based on a heat removal system using water or air which contacts the solenoid structure. The water or air is directed to flow over the solenoid structure to thereby effect heat transfer with the solenoid structure with the heated water or air being removed from contact with the solenoid structure to carry the heat away from it. The solenoids may be any suitable ferromagnetic material, but are preferably constructed from iron or PH174, which is a commonly used steel for building solenoids.

Figure 4:
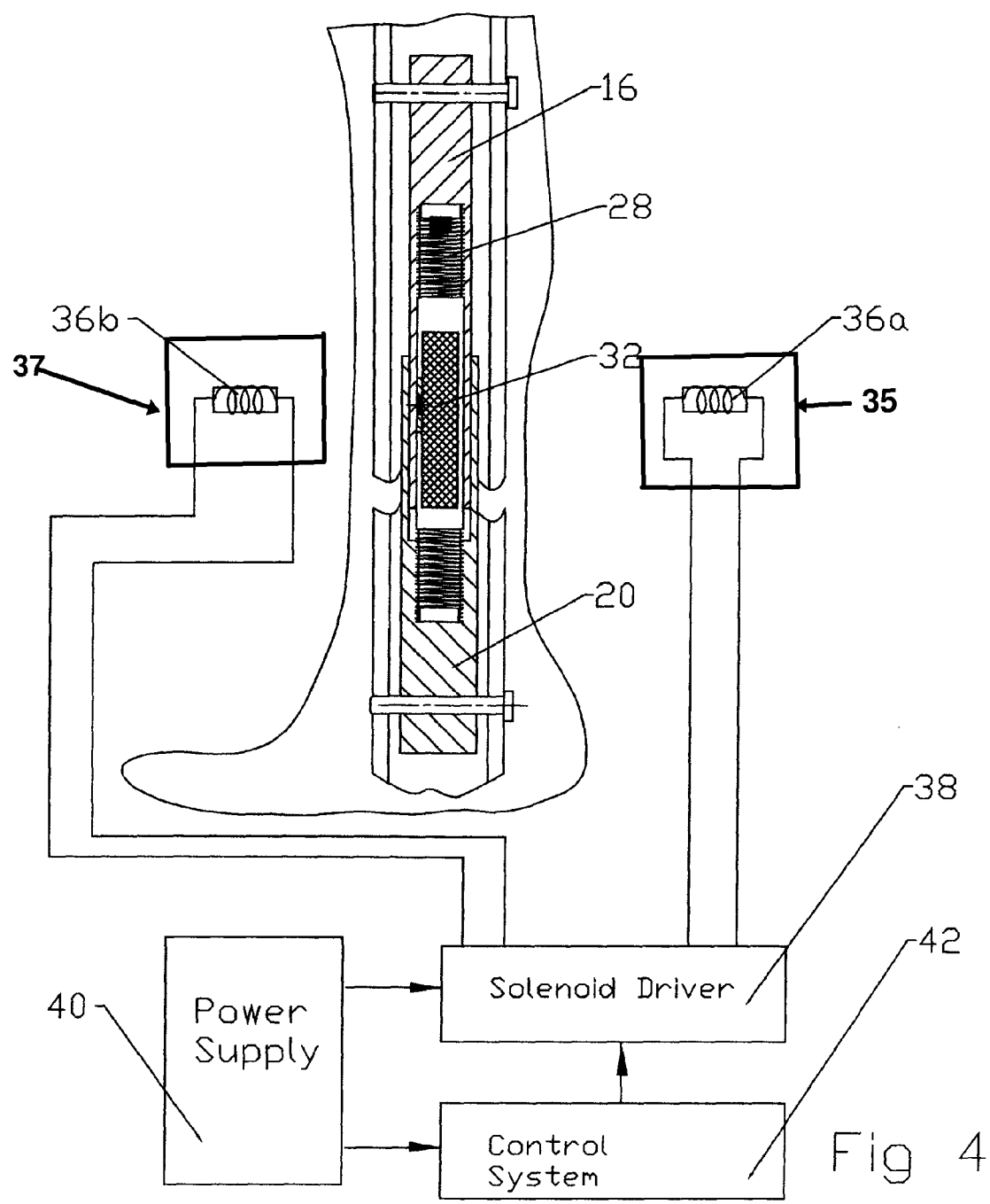
FIG. 4 shows a relative position and orientation of the implantable part and an external solenoid arrangement which interacts with the implantable part to enable bone length adjustment.

Referring now to FIG. 4, the external part of the bone length adjustment system in accordance with the invention is schematically shown. The external part includes any number of solenoids of which for simplicity, only two solenoids 36a and 36b are shown. The solenoids 36a, 36b may be arranged in a housing 35 (solenoid 36a being arranged in such a housing 35) or on a frame 37 (solenoid 36b being arranged on such a frame 37) to be positioned in the manner as shown in FIG. 4, that is, with an axis located horizontally and in a common plane. When both solenoids 36a, 36b are arranged on a frame, the frame is constructed so that in use, the solenoids 36a, 36b would be aligned with a center of the permanent magnet 32, positioned approximately equidistant from the permanent magnet 32. Both solenoids 36a and 36b are connected by wires to a solenoid driver or solenoid driving circuits 38. A power supply 40 supplies power to the solenoid driving circuits 38 and also to a control system 42 which controls the solenoid driving circuits 38. A cooling system (not shown) is also preferably mounted in the housing 35 or frame 37 to cool the solenoids.

The frame on which the solenoids 36a, 36b is mounted would also include a platform or other positioning structure to enable the part of the patient's body having the implantable part 10 to be aligned with the solenoids 36a, 36b. To this end, the frame may include one or more adjustment mechanisms for enabling adjustment of the position of the solenoids 36a, 36b and/or for enabling adjustment of the structure which positions the part of the patient's body having the implantable part 10.

Figure 5A:
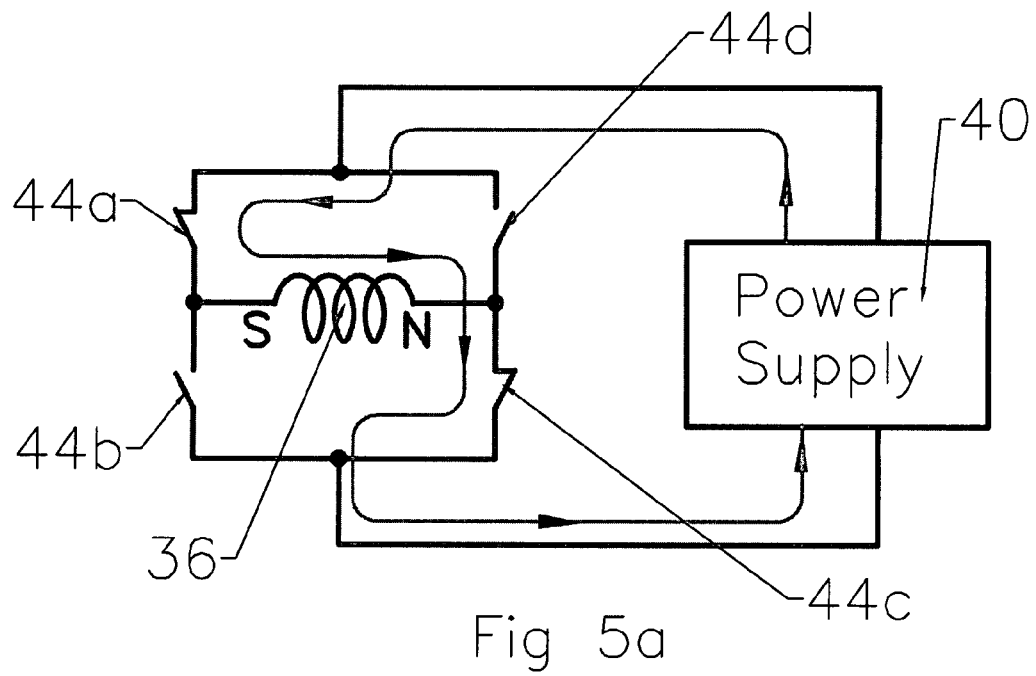
FIGS. 5a, 5b, 5c show the manner in which a magnetic field is generated using solenoids in accordance with the invention.
Figure 5B:
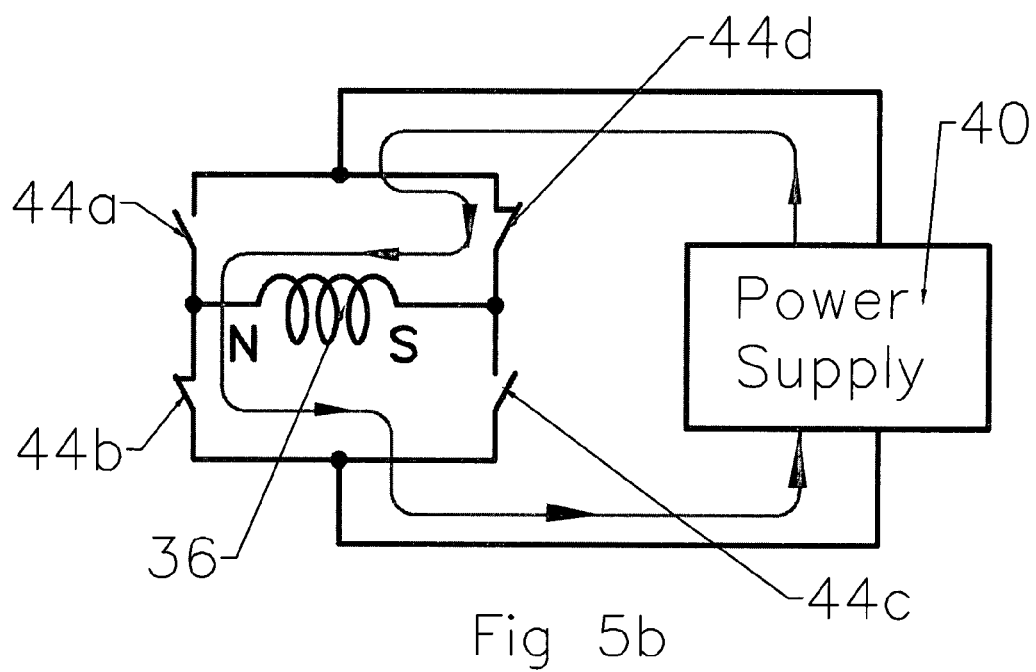

FIGS. 5a and 5b show exemplifying implementations of the solenoid driving circuits 38 that can be used in the invention. The solenoid driving circuits 38 include a number of identical driving cells configured as a circuit commonly known as an "H-bridge". Each H-bridge includes four electronically controlled switches 44a, 44b, 44c, 44d (collectively designated as 44) connected to the power supply 40. For simplicity, all connections to the control circuits are omitted, but their construction would be readily understood by one skilled in the art of solenoid driving circuits.

In one embodiment of the invention, three combinations of the ON/OFF states of the switches 44 are used, which are referred to herein as: OFF State, Forward State and Reverse State. In the OFF State, all switches 44a, 44b, 44c, 44d are open and no current flows through the solenoid 36 and no magnetic field is generated by the solenoid 36.

FIG. 5a illustrates the Forward State of an H-bridge, wherein switches 44a and 44c are closed and switches 44b and 44d are open. The current path in FIG. 5a goes from left to right, thus creating the magnetic field polarity shown as "N" for North and "S" for South poles. This polarity is for illustration purpose only.

FIG. 5b illustrates the Reverse State of an H-bridge, when switches 44a and 44c are open and switches 44b and 44d are closed. The current path in FIG. 5b goes from right to left, thus creating the magnetic field polarity shown as "N" for North and "S" for South poles which is opposite to that for the Forward State of the H-bridge shown in FIG. 5a.

Figure 5C:
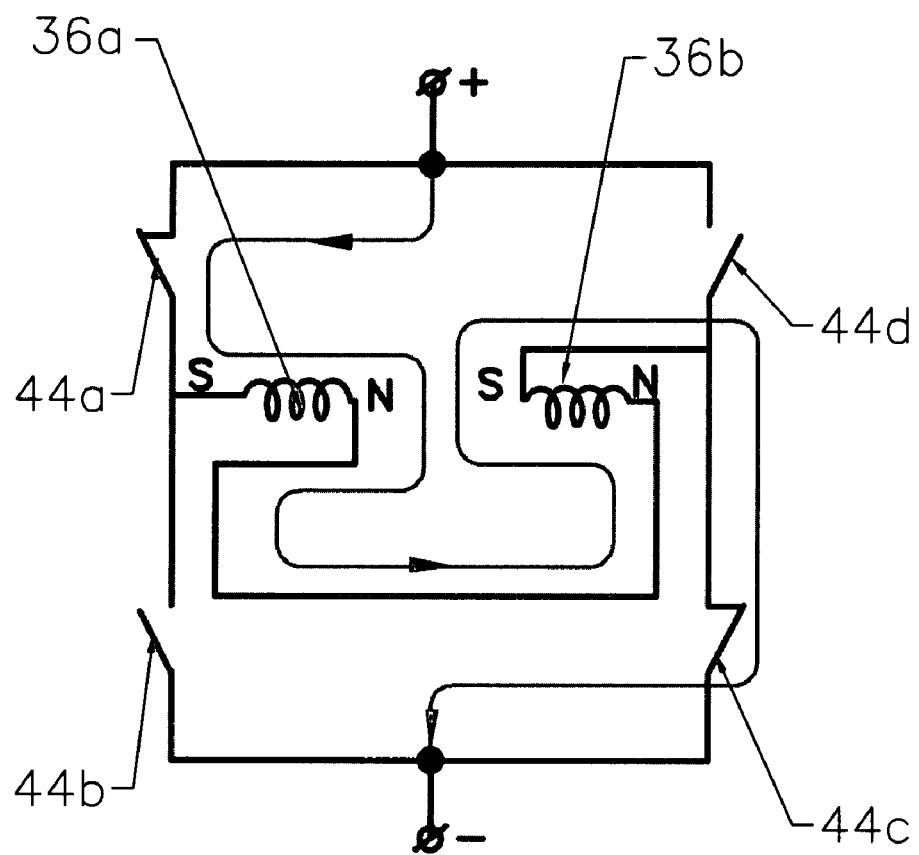

Each H-bridge is connected to two solenoids 36a, 36b in series as shown in FIG. 5c. The current through the solenoids 36a, 36b produces opposite magnetic field orientation at the nearest ends of the solenoids 36a, 36b.

In one embodiment, the external part or other mechanism for causing rotation of the magnet 32 to thereby cause rotation of the rod 28 and axial movement of the first and/or second parts 16, 20 includes a magnetic field generation mechanism having a cylindrical base including equally spaced solenoids mounted on the base. The base includes a positioning arrangement for positioning the portion of the body having the implantable part 10 such that the threaded rod 28 is located in the approximate axial center of the base and solenoids are aligned with the permanent magnet 32 in the implantable part 10 such that the longitudinal axes of the solenoids are substantially perpendicular to the longitudinal axis of the threaded rod 28 and intersects approximately the center of the permanent magnet 32.

In one embodiment, there are six solenoids and three solenoid driving circuits. In another, there are eight solenoids and four solenoid driving circuits. Thus, there may be one solenoid driving circuit for each two solenoids. In another embodiment, there may be one solenoid driving circuit for each solenoid, which is beneficial for increasing intensity of the magnetic field.

Figure 6A:
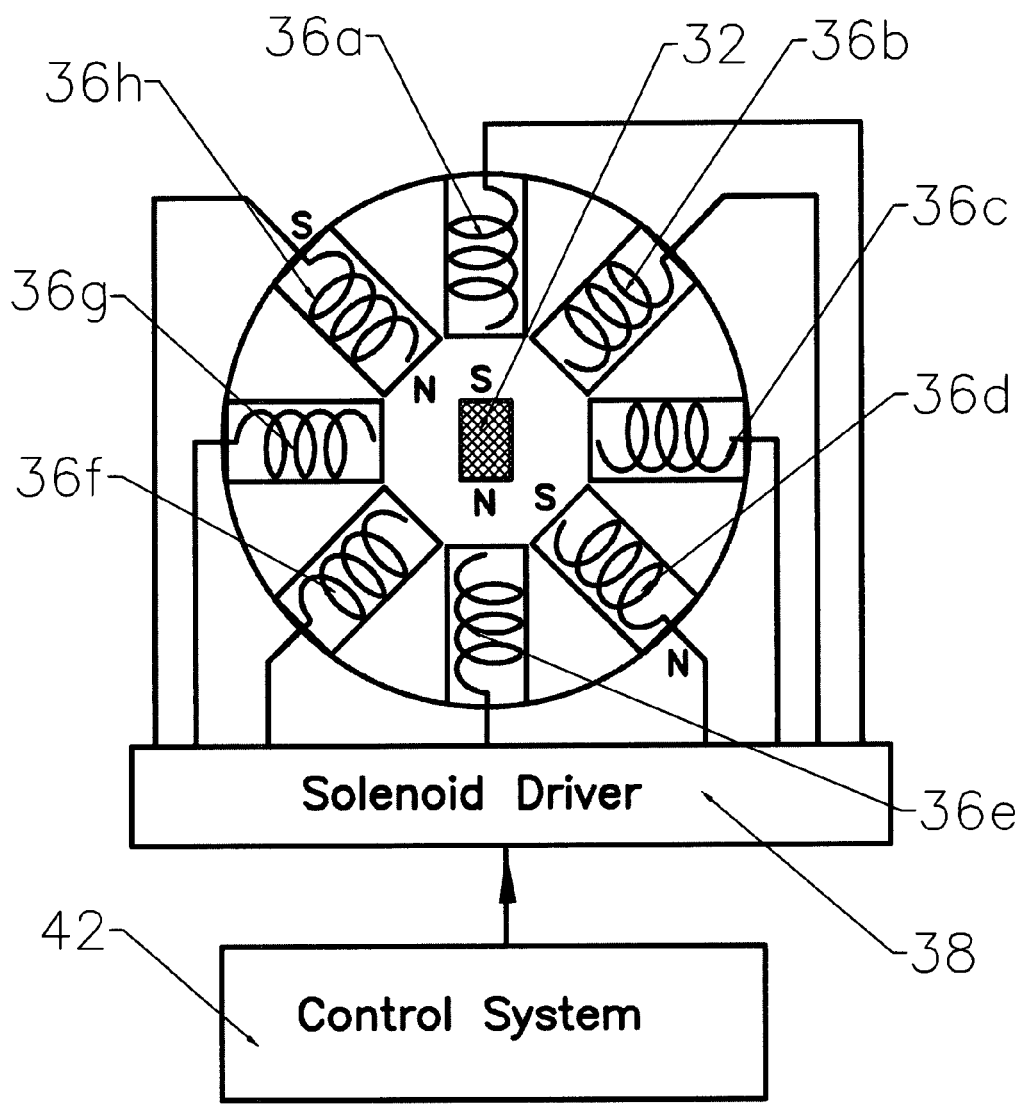
FIGS. 6a, 6b, 6c are block-diagrams of a solenoid arrangement for use in the bone adjustment arranged in accordance with the invention including eight circumferentially arranged solenoids which cooperate to enable generation of a dynamic magnetic field.

In the invention, the combination of a permanent magnet and solenoids with driving circuits constitutes a motor referred to herein as a "Stepper Motor". An exemplifying structure of one such Stepper Motor is shown in FIG. 6a. Eight solenoids 36a, 36b, 36c, 36d, 36e, 36f, 36g, 36h are placed substantially in a single, common plane crossing the approximate center of the permanent magnet 32 and incrementally spaced at 45 degrees around the vertical axis of the permanent magnet 32 (when the patient's bone with the implantable part 10 is arranged on the frame in the appropriate position relative to the solenoids 36, i.e., in a center region of the solenoids 36). Two opposite solenoids are connected in series such that the same current flowing through both solenoids creates magnetic fields of opposite polarity as shown in FIG. 5c.

Figure 6B:
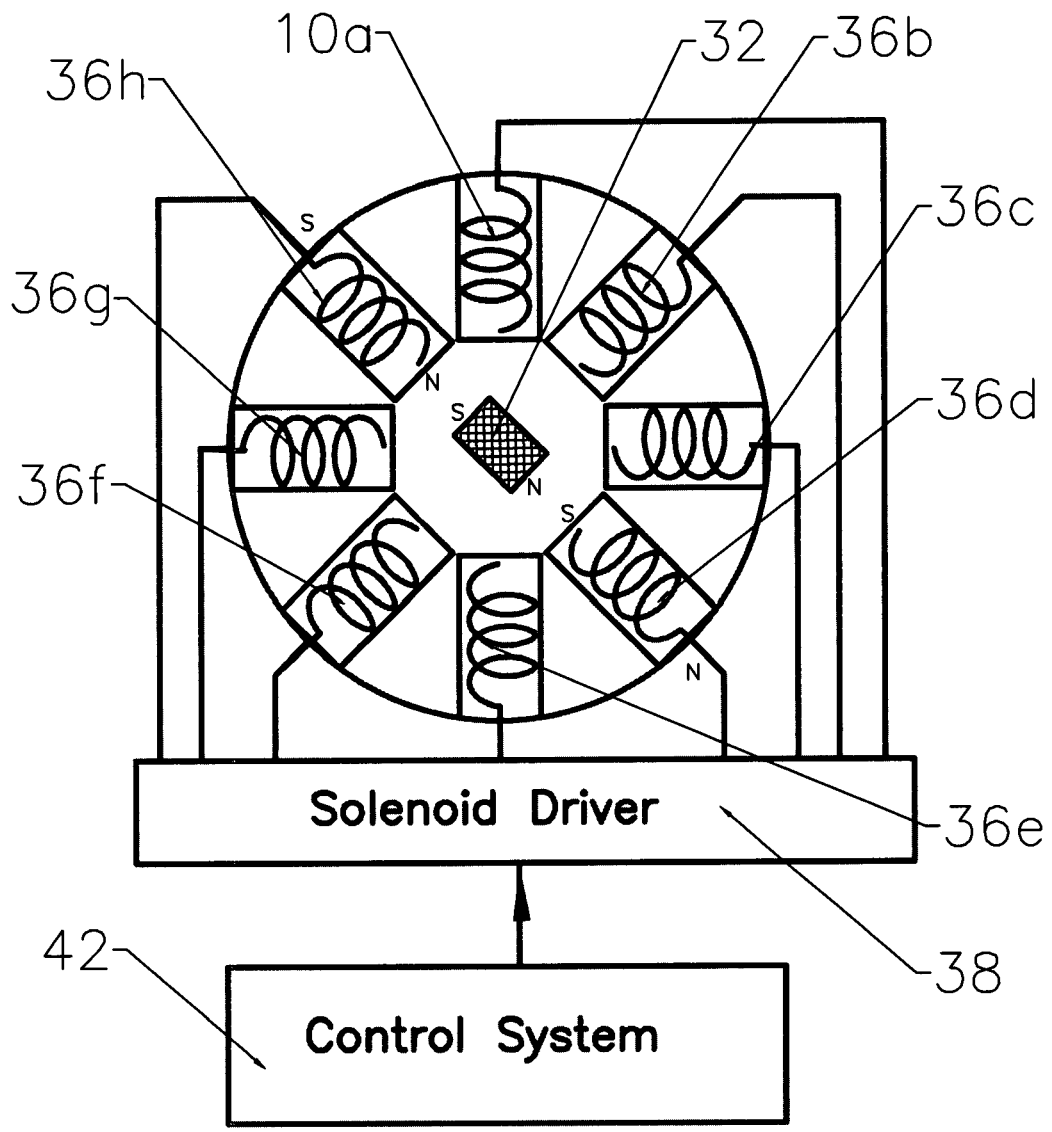

Energizing a pair of solenoids, for example solenoids 36d and 36h in FIG. 6a (bringing the H-bridge driving these solenoids into the Forward State) generates a combination of magnetic fields which interact with the field generated by the permanent magnet 32 in the implantable part 10 and create a force causing the permanent magnet 32 to move counterclockwise and stop at the position shown in FIG. 6b. Changing the active H-bridge to the OFF State stops the motion of the permanent magnet 32. The 45 degree rotation of the permanent magnet 32 (from the position shown in FIG. 6a to the position shown in FIG. 6b), and the threaded rod 28 connected thereto, is converted into axial or longitudinal motion of the first and second telescopic parts 16, 20 in the manner described above via the cooperating threads of the rod 28 and first and second parts 16, 20, thus providing compression or distraction of adjacent fractured bone ends.

Figure 6C:
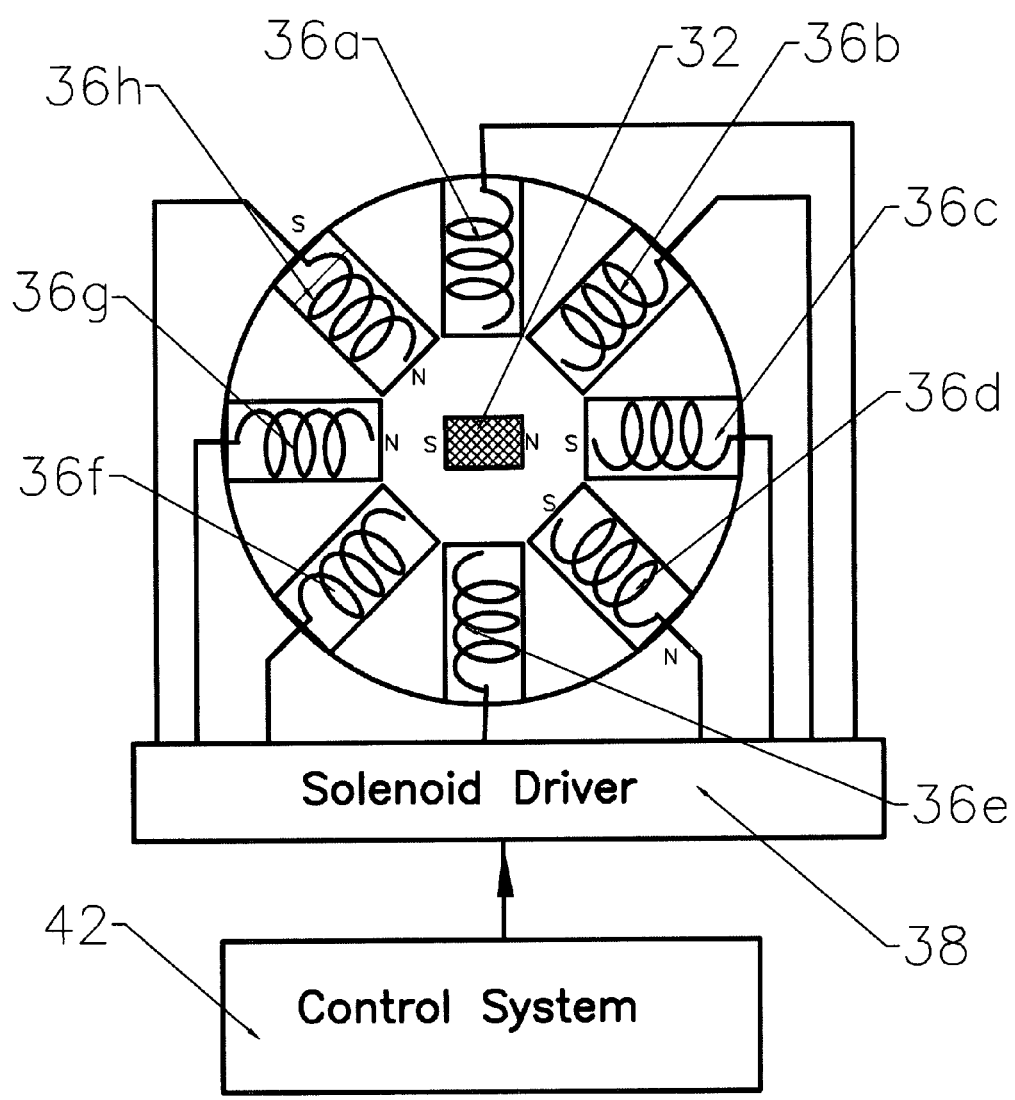

FIG. 6c shows the result of energizing coils 36g and 36c (bringing their controlling H-bridge into the ON State), which in turn causes the permanent magnet 32, and threaded rod 28 connected thereto, to move counterclockwise another 45 degrees and stop at a position 90 degrees relative to the original position shown in FIG. 6a. Energizing only one pair of solenoids provides full control over the position of the threaded rod 28 and precise and safe control over the lengthening of the fractured bone 12. The buttress formation of the threaded rod 28 prevents movement of the threaded rod 28 after all solenoids are de-energized. Other constructions of the threaded rod 28, or elements interacting therewith, to achieve this same purpose, i.e., prevent backward rotational movement of the threaded rod 28 after de-energization of the solenoids 36 can also be used in the invention.

With respect to the physics governing the rotation of the permanent magnet 32 when placed into the magnetic fields being generated by the energization of the pairs of solenoids 36, in a general form, the magnitude of torque $\tau$ acting on a magnet placed in an external magnetic field is described by a vector B and the dipole momentum μ is described as following:

$$\tau = \mu B \sin\theta \quad \text{[Formula I]}$$

wherein θ is the angle between the vector B and the longitudinal axis of the permanent magnet 32, i.e., a line between the North and South poles of the permanent magnet 32.

Figure 7:
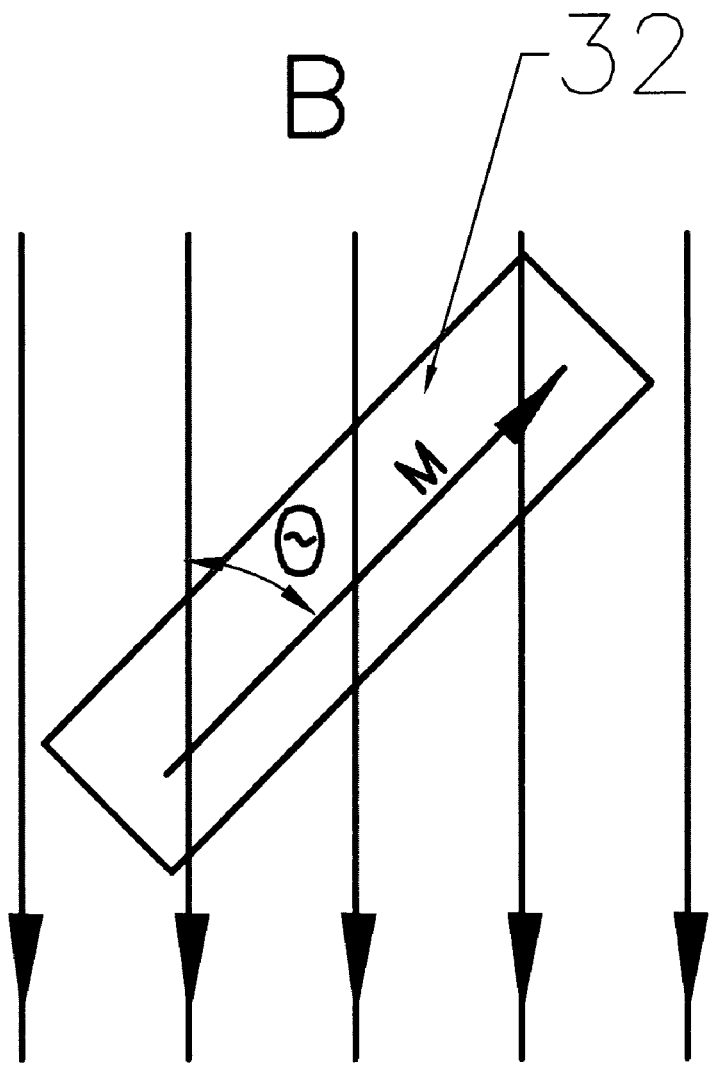
FIG. 7 shows an example of the orientation for an external magnetic field and a permanent magnet dipole momentum.

FIG. 7 shows an example of the position of a permanent magnet 32 with the resulting dipole momentum μ in the external magnetic field described by the vector B. When vector B and μ are parallel, angle θ equals zero and no torque/force develops on the permanent magnet 32. When the permanent magnet 32 approaches the point of alignment with an active pair of solenoids, the acting force drops to zero. Any external force being applied to the permanent magnet 32 changes the angle θ to a non-zero value and cause a torque τ to develop, which torque forces the permanent magnet 32 to move to and remain at the alignment point with a solenoid or solenoid pair. This feature enables reliable control over the rotation of the permanent magnet 32 and thus control over the rotation of the threaded rod 28 and thus its position. Once the permanent magnet 32 has being aligned with active solenoids, it stays at that position as long as the solenoids are energized. Even all solenoids are de-energized, the permanent magnet 32 is locked at the current position because the buttress formation on the threaded rod 28 prevents it from moving.

Since the torque τ is dependent on the angle θ many different patterns for solenoids commutation can be used. For example, in FIG. 6b, along with solenoids 36d and 36h, solenoids 36c and 36g can be energized with a relatively lower current and the same magnetic field orientation, or in addition, solenoids 36a and 36e can be energized with the opposite magnetic field orientation and a relatively lower current compared to the magnetic field orientation and current in solenoids 36d and 36h. The current through the energized solenoids can be individually shaped over the ON time for optimum torque to be developed for the permanent magnet 32 and thus also for the threaded rod 28.

The control system 42 can be implemented using a microprocessor, another processing unit or any other technique which is available for stepper motor control.

The foregoing embodiment of a bone length adjustment system is able to provide at least three modes of operation:

A. separation of bone ends.
B. compression of bone ends.
C. oscillatory mode.

The difference between the separation and compression modes is determined by the direction the threaded rod is rotated: clockwise or counterclockwise. Thus, the implantable part 10 may be implemented such that when the permanent magnet 32 is rotated clockwise, the fractured bone parts 12a, 12b move together (compression of bone ends or bones) and when the permanent magnet 32 is rotated counterclockwise, the fractured bone parts 12a, 12b move apart (separation of bone ends or bones). The opposite situation is also possible.

The oscillatory mode is a combination of the separation and compression modes, with a time interval of the switching between these two modes determining the period of oscillation. The minimum oscillation amplitude is about 45 degrees or ⅛ of full turn, in the embodiment shown in FIGS. 6a, 6b and 6c wherein there are eight solenoids 36. The minimum oscillation frequency may be close to zero cycles per second. The maximum oscillation frequency depends on mechanical characteristics of the threaded rod assembly 28, electrical characteristics of the solenoids 36, and a controlling algorithm of the control system 42. In practice, it has been considered that the maximum oscillation frequency may be in an order of about 100 Hz to about 1000 Hz. Oscillation is controlled by control system 42 via the appropriate energization of the solenoids 36.

Figure 8:
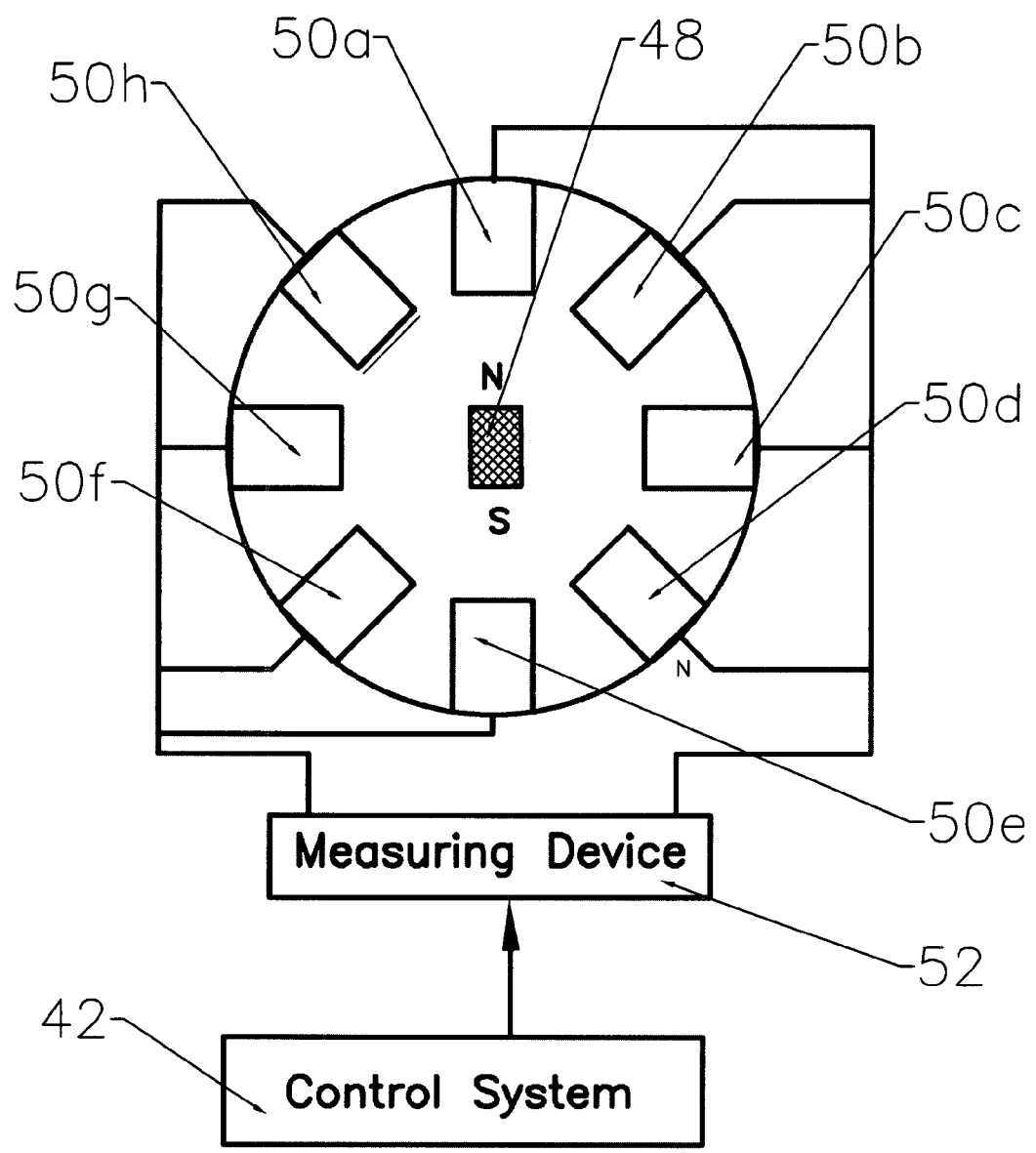
FIG. 8 shows a block diagram of a magnet position measuring system for use in the invention.

Referring now to FIG. 8, in order to improve reliability and accuracy of the bone length adjustment process described above, a positioning feedback loop can be implemented. To this end, a position measuring system is provided and includes a small permanent magnet 48, which is embedded into, or otherwise connected to, the threaded rod 28 as shown in FIGS. 1a and 1b and a plurality of magnetic field sensors 50, such as eight magnetic field sensors 50a, 50b, 50c, 50d, 50e, 50f, 50g and 50h as shown in FIG. 8. The magnetic field sensors 50 are arranged in a configuration similar to the configuration of solenoids 36 as shown in FIGS. 6a, 6b and 6c. Each sensor 50 is capable of measuring the magnetic field intensity and polarity. A signal from the sensor 50 is preferably processed and conditioned by a measuring device 52 which sends this information in the form of signals to the control system 42. Data about the position of the positioning magnet 48 is received by the control system 42 is analyzed in order to calculate the actual position of the positioning magnet 48. This information is necessary to automate the bone adjustment process, i.e., determine the appropriate energization of the solenoids to provide a dynamic rotational magnetic field which will generate the desired axial or longitudinal movement of the first and/or second parts 16, 20. Sensors 50 may be Hall-effect-based sensors capable of magnetic field sensing, as well as other appropriate sensors.

Figure 9A:
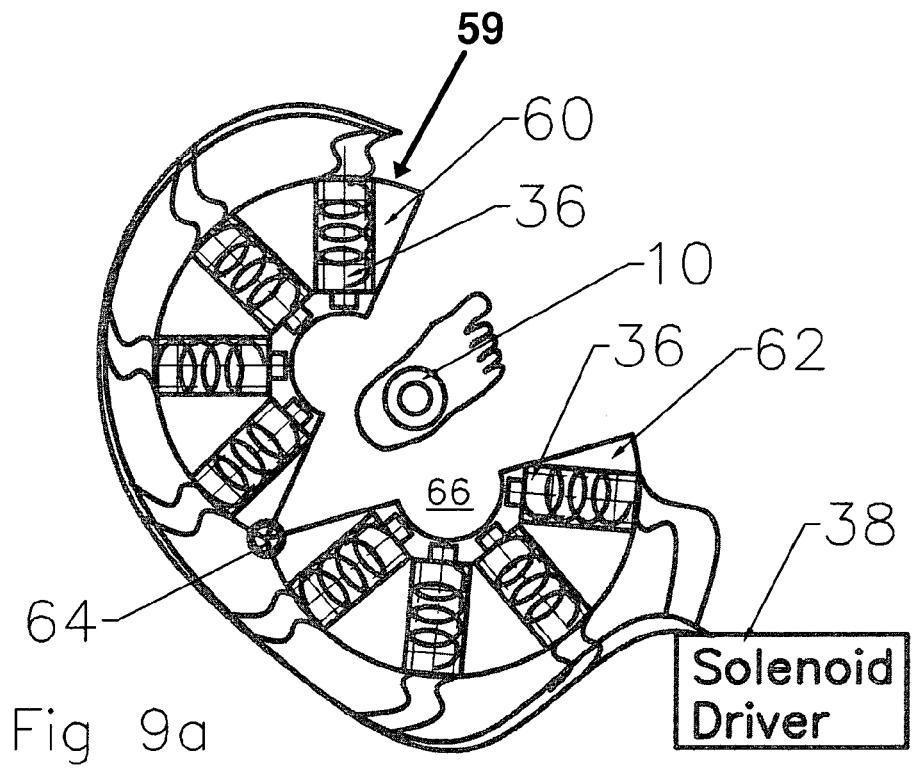
FIG. 9a shows an embodiment of the external solenoid arrangement which can be pivoted open to enable a patient to place a bone having the implantable part into a center area thereof.
Figure 9B:
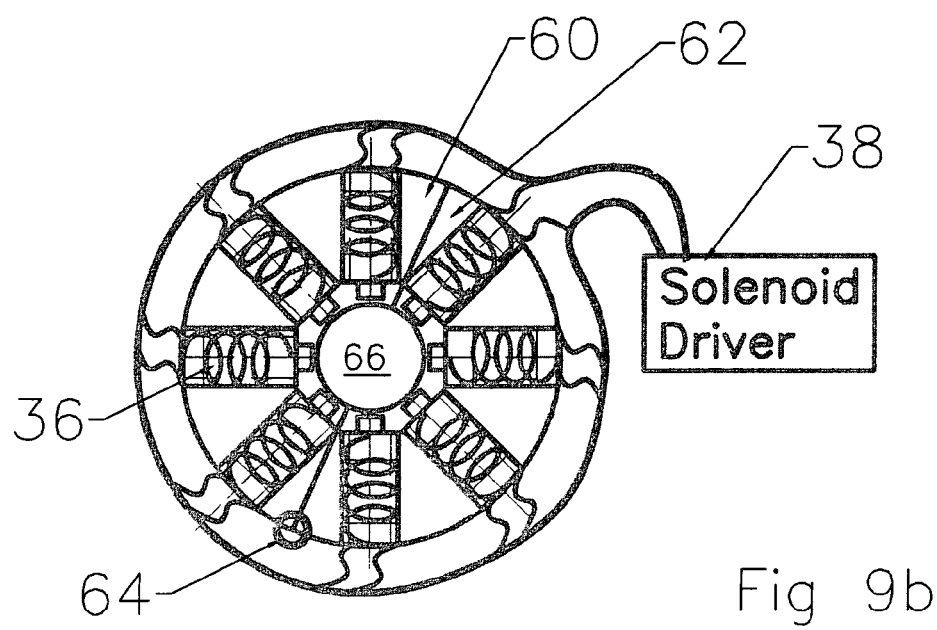
FIG. 9b shows the external solenoid module of FIG. 9a in a closed position.

FIGS. 9a and 9b show an embodiment wherein the external solenoid arrangement is arranged on a pivotal frame 59. The frame 59 includes a first frame part 60 on which four solenoids 36 are arranged and a second frame part 62 on which another four solenoids 36 are arranged. Frame parts 60, 62 pivot relative to one another at a pivot point 64. Solenoids 36 are arranged in a common plane. By constructing the frame 59 in this manner, access to the center region 66 defined between the solenoids 36 is considerably easier.

In use, the frame parts 60, 62 would be pivoted apart from one another and the patient would place the bone 12 having the implantable part 10 into the center region 66, e.g., the leg or foot as shown. One or both frame parts 60, 62 are then pivoted into the closed position and possibly locked into this closed position during energization of the solenoids 36. The solenoid driving circuit 38 is then controlled by control system 42 (not shown in these figures) to generate the dynamic magnetic field which causes rotation of the permanent magnet 32 in the implantable part 10 and thus rotation of the threaded rod 28 which in turn causes axial or longitudinal movement of the parts 16, 20 resulting in adjustment in the length of the fractured bone or adjustment of the distance between connected bone parts.

Variations to the bone length adjustment technique described above are envisioned. For example, the permanent magnet 28 can, instead of being implanted into the intramedullary cavity in a bone, can be used external to or outside of a bone. This technique may be used for example, for correction of skull bones deformation and other flat bones corrections, like the clavicle.

For an internal body use, but exterior of the bone, instead of an implantable part implantable into a cavity of a bone, there would be a biocompatible part which may be positioned partly or entirely around the fractured bone with one telescoping part connected to one part of the bone and the other telescoping part connected to the other part of the fractured bone. A permanent magnet would be connected to a rod or other elongate member extending between these two parts and be connected to the two telescoping parts, e.g., via cooperating threads as described above. The bone adjustment process would be substantially the same as described above wherein the permanent magnet is positioned between solenoids to cause rotation of the magnet which translates into axial or longitudinal movement of the telescoping parts.

Figure 10A:
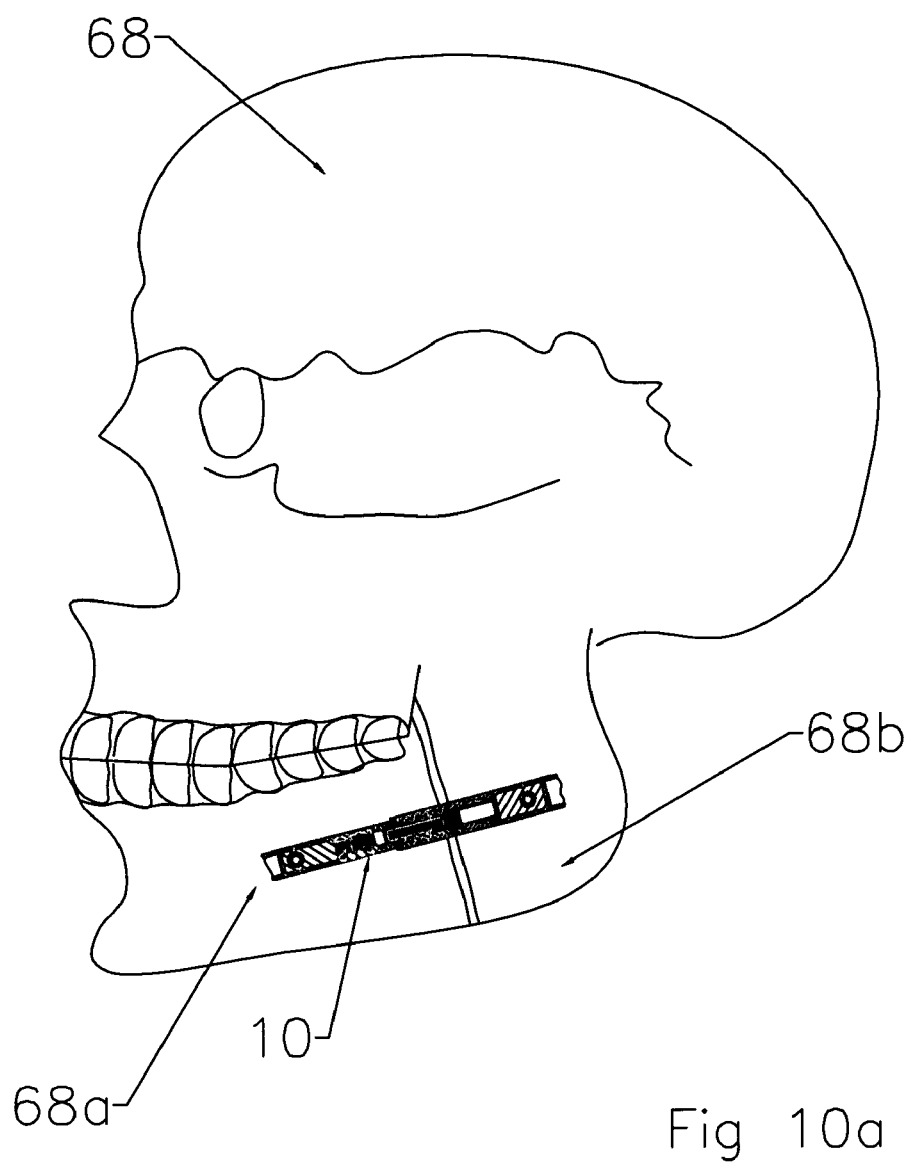
FIG. 10a shows an embodiment wherein the implantable part of a bone length adjustment system of FIG. 1b is attached to a fracture bone in a human skull (mandible).

In this regard, referring now to FIGS. 10a and 10b, the first part 16 of the implantable part 10 is shown attached via nail 18 to a first part 68a of a fractured skull 68 while the second part 20 of the implantable part 10 is attached via nail 22 to a second part 68b of the fractured skull 68. In this embodiment, implantable part 10 is not situated in a cavity of a bone but rather is attached to the side or edge of the skull bone 68, yet is still internal to the body. Using implantable part 10, it is possible to adjust the distance between the fractured bone parts 68a, 68b in order to properly set the fractured bone or possibly to enable correction of skull deformations. Otherwise, the implantable part includes the same structure as in any of the embodiments described herein, including the embodiments shown in FIG. 1a and FIG. 1b. Indeed, the implantable part shown in FIG. 10 is otherwise similar to that shown in FIG. 1b.

The same type of arrangement could also be arranged external of the bone and body, with one telescoping part being connected through skin to one part of the fractured bone and the other telescoping part being connected through skin to the other part of the fractured bone.

Figure 11:
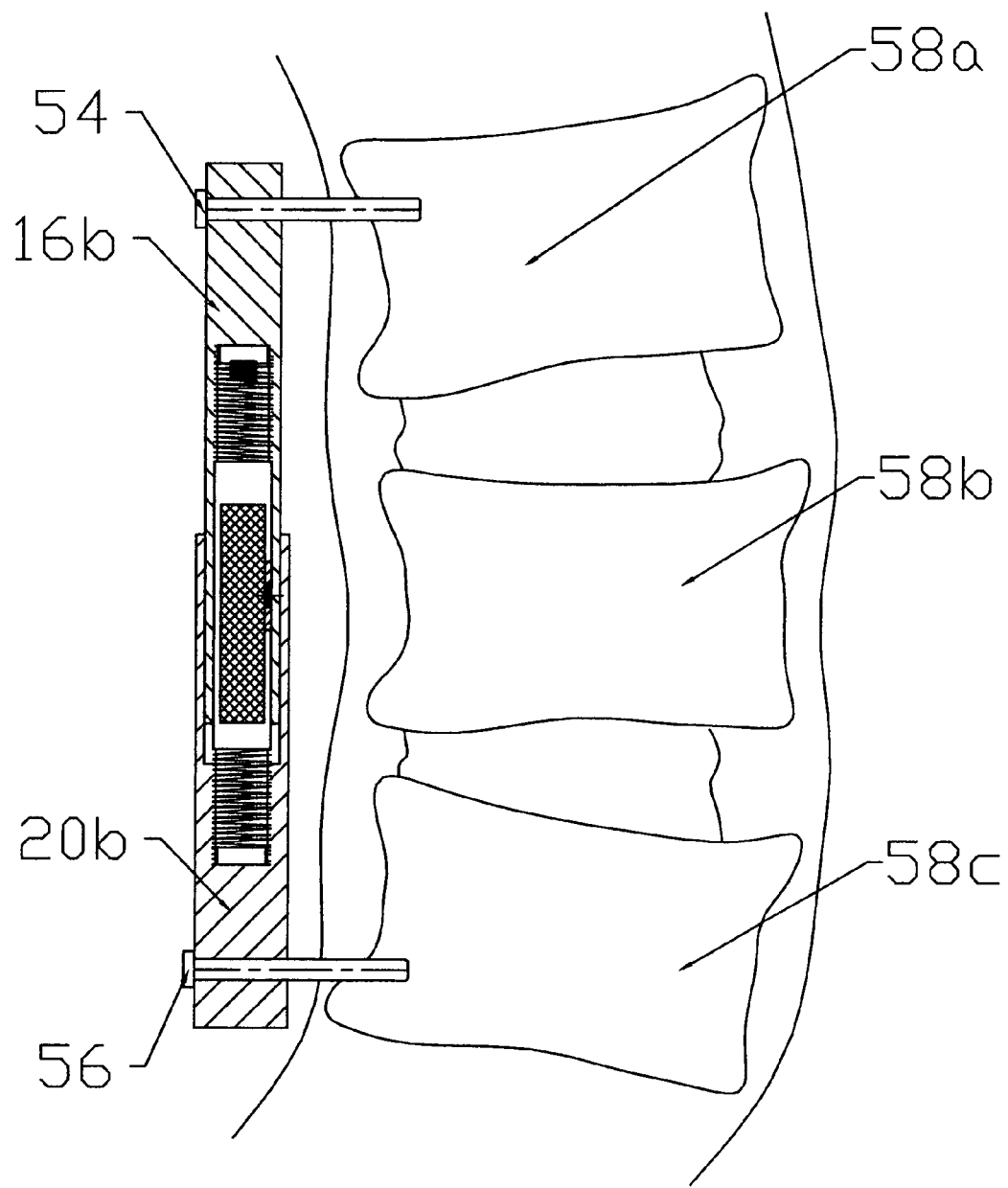
FIG. 11 shows use of the implantable part of the bone length adjustment device shown in FIG. 1a for adjustment of a spine.

Referring now to FIG. 11, the present invention can also be used for adjustment of the spine, for example, to correct for spinal deformities. In this case, one telescoping part 16B of the implantable part of the bone adjustment arrangement in accordance with the invention is attached to a bone 58a in the spinal column, e.g., via a screw 54, and another telescoping part 20B is attached to another bone 58c in the spinal column, e.g., via a screw 56. The bones of the spinal column to which the telescoping parts 16B, 20B are attached may be adjacent one another or separated from one another by another bone 58b such as shown in FIG. 11. Otherwise, the implantable part includes the same structure as in any of the embodiments described herein, including the embodiments shown in FIG. 1a and FIG. 1b. Indeed, the implantable part shown in FIG. 11 is otherwise similar to that shown in FIG. 1a.

The process for adjustment of the spine is the same as described above for adjustment of other bones, i.e., involves controlled use of the external arrangement of solenoids. In this embodiment, the implantable part 10 is able to cause an adjustment of the distance between bones 58a and 58c.

It is important to note that in the use depicted in FIG. 11, the bone length adjustment system is not used to adjust the length of a single bone which has fractured but rather is used to adjust the relative distance between bones. Similarly, any of the embodiments of the implantable part described herein can be used to adjust the distance between two different bones.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

The invention claimed is:

1. An arrangement for adjusting a length or distance between bone parts when coupled to the bone parts, comprising:

a telescoping device comprising:
    a first part adapted to be coupled to a first bone part and including a first cavity,
    a second part adapted to be coupled to a second bone part and including a second cavity, said first and second parts of said telescoping device being axially movable relative to one another, said first cavity facing said second part, said second part being situated at least partially in said first cavity and partly slidable therein,
    a rod arranged in said first and second cavities defined by said first and second parts of said telescoping device, respectively, and having a first end portion movable relative to said first part of said telescoping device and a second end portion movable relative to said second part of said telescoping device, and
    at least one magnet arranged in connection with said rod, said rod being rotationally coupled to an interior of both of said first and second parts of said telescoping device such that rotation of said rod is translated into axial movement of said first part and second part of said telescoping device; and
a magnetic field generating mechanism that causes rotation of said at least one magnet to thereby cause rotation of said rod and axial movement of at least one of said first and second parts of said telescoping device,
    said magnetic field generating mechanism comprising a frame and a solenoid arrangement arranged outside of said telescoping device and arranged to generate a dynamic magnetic field around an operative region to cause rotation of said at least one magnet when situated in said operative region,
    said solenoid arrangement comprising a plurality of pairs of solenoids housed in said frame,
    said solenoids being arranged in a common plane and each of said pairs of solenoids having a common axis,
    said frame being arranged to position a portion of the body having said telescoping device such that said at least one magnet is aligned with and between said pairs of solenoids.

2. The arrangement of claim 1, wherein said telescoping device includes a movement conversion mechanism that converts rotational movement of said rod into axial or longitudinal movement of at least one of said first and second parts.

3. The arrangement of claim 2, wherein said movement conversion mechanism comprises a thread arranged at each end of said rod and engaged with a threaded surface having threads defined in each of said first and second cavities, said threads of said first part being in an opposite direction from said threads of said second part and said threads at said ends of said rod being in opposite directions.

4. The arrangement of claim 2, wherein said movement conversion mechanism comprises a thread arranged at one end of said rod, a shoulder arranged at the other end of said rod, a cavity in said first part facing said second part and engaged with said thread of said rod, and at least one bearing interposed between said shoulder and an inner surface of a cavity in said second part facing said first part and attached to said second part, said shoulder pushing or pulling said at least one bearing to convert rotation of said rod into axial movement of said second part.

5. The arrangement of claim 1, further comprising:
    a first fixing mechanism adapted to fix said first part of said device to the first bone part; and
    a second fixing mechanism adapted to fix said second part of said device to the second bone part.

6. The arrangement of claim 5, wherein said first fixing means comprise a nail and said second fixing means comprise a nail.

7. The arrangement of claim 1, wherein said first and second parts of said device are made of non-magnetic material.

8. The arrangement of claim 1, wherein said rod is threadingly engaged with only said first part.

9. The arrangement of claim 1, wherein said first and second parts of said telescoping device are cylindrical and said second cavity is a cylindrical cavity into which a portion of said first part is situated and said portion of said first part partly sliding in said cylindrical cavity.

10. The arrangement of claim 1, wherein said magnetic field generating mechanism is arranged to generate a clockwise or counterclockwise dynamic magnetic field such that said at least one magnet rotates in a clockwise or counterclockwise direction causing said first and second parts to move either closer to one another to effect a reduction in a length of said telescoping device or apart from one another to effect an increase in a length of said telescoping device.

11. The arrangement of claim 1, further comprising at least one solenoid driver for driving at least one of said solenoids and a control system for determining how to control said at least one solenoid driver to effect a desired rotation of said at least one magnet to provide a desired axial movement of said first and/or second parts.

12. The arrangement of claim 11, wherein each of said at least one solenoid driver includes an "H-bridge" having four electronically controlled switches and a power supply for supplying current through said switches to control a direction of current flow through said at least one solenoid.

13. The arrangement of claim 11, wherein said control system is arranged to energize said at least one solenoid in sequence to effect stepwise rotation of said at least one magnet.

14. The arrangement of claim 11, further comprising a positioning magnet arranged in connection with said rod and magnetic field sensing means arranged in connection with said frame for detecting said positioning magnet, said control system being arranged to control said at least one solenoid driver in consideration of the position of said positioning magnet as detected by said magnetic field sensing means.

15. The arrangement of claim 1, wherein said frame has a first part pivotable relative to a second part to enable access to a center region of said frame in which the portion of the body having said telescoping device is positionable.

16. The arrangement of claim 1, wherein said first and second parts are arranged to allow only axial movement of said first and second parts and prevent rotation of said first and second parts relative to one another.

17. The arrangement of claim 1, wherein said solenoids are arranged to generate a clockwise or counterclockwise dynamic magnetic field while said solenoid arrangement is stationary by applying a variable electric field to said solenoid arrangement.

18. The arrangement of claim 1, wherein said solenoids are spaced apart from one another.

19. The arrangement of claim 1, wherein said at least one magnet is arranged in connection with said rod such that an axis between poles of said at least one magnet is substantially parallel to an axial axis of said rod.

20. A method for adjusting a length of a bone or distance between bone parts, comprising:

connecting a first part of a telescoping device to a first bone, the first part including a first cavity;

connecting a second part of the telescoping device to a second bone part, the first and second parts being axially movable relative to one another to thereby cause a change in the relative position of the first and second bone parts, the second part including a second cavity;

arranging a rotatable rod in the first and second cavities defined by the first and second parts;

connecting the rod to an interior of both the first and second parts such that rotation of the rod is translated into axial movement of at least one of the first and second parts relative to one another;

connecting at least one magnet to the rod;

generating a magnetic field around the at least one magnet, via a magnetic field generating mechanism, to cause rotation of the at least one magnet to thereby cause rotation of the rod and axial movement of at least one of the first and second parts; and controlling the generation of the magnetic field to provide controlled adjustment of the axial movement of the at least one of the first and second parts and thus controlled adjustment of the length of the telescoping device, the magnetic field generating mechanism comprising a frame and a solenoid arrangement arranged outside of the telescoping device and arranged to generate a dynamic magnetic field around an operative region to cause the rotation of the at least one magnet when situated in the operative region, the solenoid arrangement comprising a plurality of pairs of solenoids housed in the frame, the solenoids being arranged in a common plane and each of the pairs of solenoids having a common axis, the frame being arranged to position a portion of the body having the telescoping device such that the at least one magnet is aligned with and between the pairs of solenoids.

21. The method of claim 20, further comprising arranging the first and second parts of the telescoping device in an intramedullary cavity of a fractured bone such that the first part is connected to one part of the fractured bone and the second part is connected to another part of the fractured bone on the opposite side of the fracture.

22. The method of claim 20, further comprising arranging the first and second parts of the telescoping device external to and against an outer side of fractured bone such that the first part is connected to one part of an exterior of the fractured bone and the second part is connected to another part of the exterior of the fractured bone on the opposite side of the fracture.

23. The method of claim 20, further comprising arranging the first and second parts of the telescoping device external to and against a spine such that the first part is connected to one spinal bone and the second part is connected to another spinal bone.

24. The method of claim 20, wherein the step of connecting the second part of the telescoping device to the second bone part comprises connecting the second part of the telescoping device to a different part of the same bone to which the first part of the telescoping device is connected such that the first and second parts of the telescoping device are connected to the same bone.

25. The method of claim 20, wherein the step of connecting the rod to an interior of both the first and second parts comprises:
 arranging a first threaded portion at a first end of the rod;
 arranging a second threaded portion at a second end of the rod, the second threaded portion having an opposite thread direction than the first threaded portion of the rod; and
 engaging the first threaded portion of the rod with a thread on an inner surface of the first part defining the first cavity; and
 engaging the second threaded portion of the rod with a thread on an inner surface of the second part defining the second cavity.

* * * * *